US00PP31197P3

(12) United States Plant Patent
Fernández

(10) Patent No.: US PP31,197 P3
(45) Date of Patent: Dec. 10, 2019

(54) ***RUBUS* PLANT NAMED 'EMR 20171'**

(50) Latin Name: ***Rubus idaeus* hybrid**
Varietal Denomination: emr 20171

(71) Applicant: East Malling Services Ltd, Kent (GB)

(72) Inventor: Felicidad Fernández, Maidstone (GB)

(73) Assignee: EAST MALLING SERVICES, LTD, Kent (GB)

( * ) Notice: Subject to any disclaimer, the term of this patent is extended or adjusted under 35 U.S.C. 154(b) by 0 days.

(21) Appl. No.: 15/932,076

(22) Filed: Jan. 29, 2018

(65) Prior Publication Data

US 2018/0220571 P1 Aug. 2, 2018

(30) Foreign Application Priority Data

Jan. 31, 2017 (QZ) ..... PBR 20170261

(51) Int. Cl.
*A01H 5/08* (2018.01)
*A01H 6/74* (2018.01)

(52) U.S. Cl.
USPC ..... Plt./204
CPC ..... *A01H 6/7499* (2018.05)

(58) Field of Classification Search
USPC ..... Plt./204
See application file for complete search history.

(56) References Cited

PUBLICATIONS

UPOV hit on *Rubus* plant named 'Emr 20171', QZ PBR 20170261, filef Feb. 1, 2017.*

* cited by examiner

*Primary Examiner* — Anne Marie Grunberg
(74) *Attorney, Agent, or Firm* — Penny J. Aguirre

(57) ABSTRACT

A new cultivar of *Rubus idaeus* hybrid plant, 'emr 20171', that is characterized by its attractive, bright colored blunt conical shaped fruit that is well displayed and easy to detach, its excellent shipping properties and shelf-life that make an ideal variety for large-scale commercial production in the primocane season and as a 'double cropper'; produced both on primocanes and floricanes following a period of natural or enforced dormancy, its vigorous primocanes that are held erect with developed lateral branches, its spines and thorns that are not prominent enough to interfere with picking and/or pruning, its berries with excellent eating quality both at harvest and after shipping, its berries that are sweet, aromatic, firm, and juicy with a good balance of sugar and acid, and its berries that do not darken and retain good texture after being chilled for transport.

2 Drawing Sheets

Botanical classification: *Rubus idaeus* hybrid.
Cultivar designation: 'emr 20171'.

BACKGROUND OF THE INVENTION

The present invention relates to a new and distinct cultivar of raspberry plant, botanically thought to be of hybrid origin with *Rubus idaeus* and other species in its ancestry. 'emr 20171' will be referred to hereinafter by its cultivar name, 'emr 20171'. 'emr 20171' is a new raspberry plant grown for fruit production.

'emr 20171' arose from an on going breeding program conducted by the Inventor in East Malling, Kent, United Kingdom. The objectives of the breeding program are to develop new cultivars of *Rubus* with outstanding fruit quality in primocane fruiting varieties.

'emr 20171' was discovered by the Inventor as a chance seedling in August of 2007 in a trial bed that had been planted with seeds of unknown parentage. 'emr 20171' underwent further trials in the United Kingdom and Spain from 2008 to 2017 to verify its unique and stable characteristics.

Asexual propagation of the new cultivar was first accomplished by the Inventor by root cuttings in East Malling, Kent, United Kingdom in winter of 2007. Asexual propagation of the new cultivar by root cuttings, stem cuttings, and tissue culture using meristem tissue has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'emr 20171' as a new and unique cultivar of *Rubus*.

1. 'emr 20171' exhibits attractive, bright colored blunt conical shaped fruit that is well displayed and easy to detach.
2. 'emr 20171' exhibits excellent shipping properties and shelf-life that make an ideal variety for large-scale commercial production in the primocane season and as a 'double cropper'; produced both on primocanes and floricanes following a period of natural or enforced dormancy.
3. 'emr 20171' exhibits vigorous primocanes that are held erect with developed lateral branches.
4. 'emr 20171' exhibits spines and thorns that are not prominent enough to interfere with picking and/or pruning.
5. 'emr 20171' exhibits berries with excellent eating quality both at harvest and after shipping.

6. 'emr 20171' exhibits berries that are sweet, aromatic, firm, and juicy with a good balance of sugar and acid.
7. 'emr 20171' exhibits berries that does not darken and retain good texture after being chilled for transport.

'emr 20171' can be compared to *Rubus* cultivars 'Kweli' (not patented) and 'Imara' (not patented). 'Kwell' and 'Imara' are similar to 'emr 20171' in having similar plant habits, berry yields, blunt conical shaped fruit, excellent commercial quality and good shelf lives. 'Kwell' differs from 'emr 20171' in having canes that have more thorns, cane surface bloom and fruit that is slightly darker in color and less sweet. 'Imara' differs from 'emr 20171' in having noticeable darker fruit that is less sweet, and in having a slightly later harvest season.

BRIEF DESCRIPTION OF THE DRAWINGS

The accompanying colored photographs illustrate the overall appearance and distinct characteristics of the new *Rubus*. The photographs were taken of plants about 3 years in age as grown in peat based trough containers in tunnels in East Malling, Kent, United Kingdom.

The photograph in FIG. 1 provides a view of the fruiting canes of 'emr 20171' showing berries at different stages of maturation.

Figure 1:
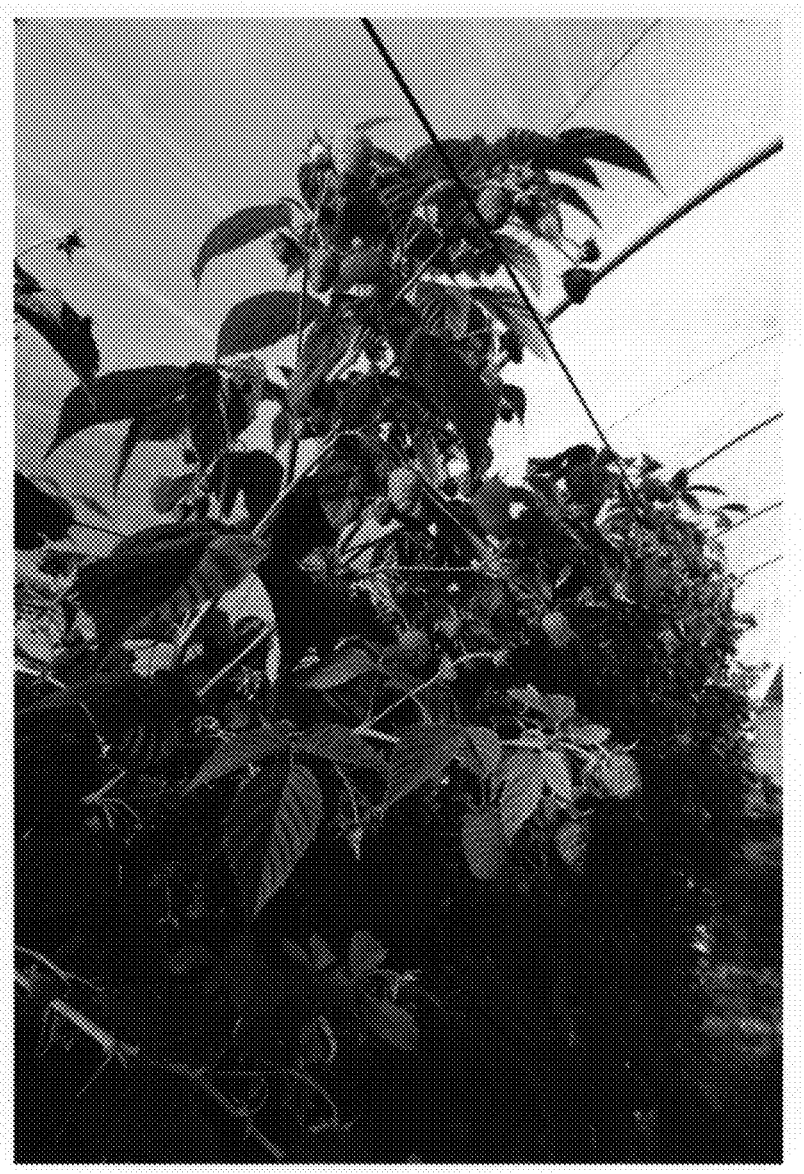
Figure 2:
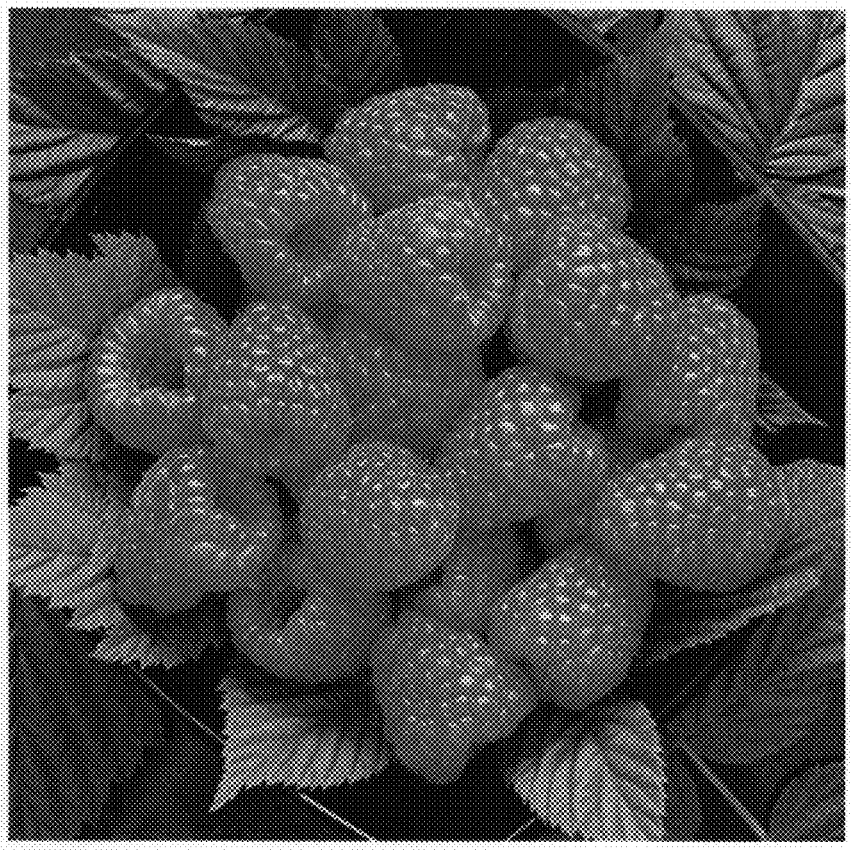

The photograph in FIG. 2 provides a close-up view of the fruit of 'emr 20171'.

Figure 3:
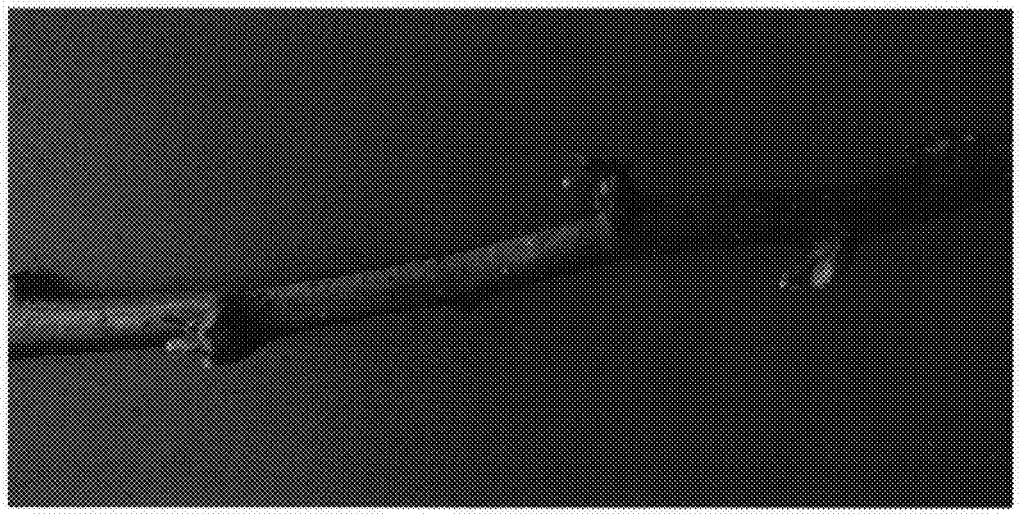

The photograph in FIG. 3 provides a view of a dormant cane of 'emr 20171'.

The colors in the photographs are as close as possible with the photographic and printing technology utilized. The colors in the photograph may differ slightly from the color values cited in the detailed botanical description, which accurately describe the colors of the new *Rubus*.

DETAILED BOTANICAL DESCRIPTION OF THE PLANT

The following is a detailed description of 2-year-old plants of the new cultivar as grown under Spanish tunnels in trough containers in East Malling, Kent, United Kingdom. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used. This variety is primarily grown as a primocane so the descriptions are focused on the year cane toward the end of the summer when in full production.

General description:

*Blooming period.*—As a floricane; mid to late-season flowering from late May to mid-July, as a primocane; mid-season flowering from late July to late October in southern England.

*Plant habit.*—Perennial, upright with well-developed laterals and pronounced branching on the primocanes.

*Height and spread.*—Can vary significantly depending on pedoclimatic conditions, irrigation management and fertilizer regime, for plants grown on a course peat-based substrate in a typical year; the primocanes reach between 1.4 and 1.7 m height, typically canes grow to have between 21 and 40 nodes (average of 32) branched canes typically have a spread of 1 to 1.5 m with some of the longest laterals exceeding 0.5 m in length (average lateral length 24 cm).

*Internode length.*—Average of 3.76 cm (varying between 1.5 to 5 cm) depending of position in the cane and individual cane vigor.

*Hardiness.*—This trait has not been fully characterized in a range of cold weather climates but the plants can successfully grow in England (U. K hardiness Zone 8) and areas of central Europe (U. K. Hardiness Zone 7).

*Diseases and pests.*—This variety has not shown any resistance to pest or diseases and it is intermediately susceptible to *Verticillum* wilt (caused by *Verticillium dahliae*) in field conditions of southern England.

*Root description.*—Fibrous and vigorous.

*Branching habit.*—Freely branching.

*Propagation.*—Root cuttings, stem cuttings and tissue culture.

*Growth rate.*—Vigorous.

Cane description (primocanes measured towards the end of the growing season):

*Cane size.*—Can vary significantly depending on pedoclimatic conditions and fertilizer regime, for plants grown on a course peat-based substrate in a typical year the primocane canes can reach between 1.4 and 1.7 m height but can be as low as 1.25 m under moderate stress, average width at mid stem is 7.4 mm.

*Stem color.*—The new canes are pale green 145C to 145 B, towards the end of the growing season, they mature to a darker color at the base (166A) that fades in to the lighter green shades (146 D) toward the top of the cane, the dormant cane is primarily 166A in color, typically, under conventional polythene tunnels the canes develop only a mild blush that ranges from 184A and 184B.

*Stem surface.*—Glabrous with spines that are not typically too prominent, spine color 183B.

*Stipules.*—2 per petiole, slightly pubescent but mainly smooth, an average of 10 mm in length, lanceolate in shape, color 144A.

Foliage description (descriptions are of basal leaves of the fruiting primocanes):

*Time of vegetative bud burst.*—In the floricane, bud burst is typically in early to mid May but it can vary significantly from year to year.

*Leaf shape.*—Ovate in overall form.

*Leaf division.*—Typically 3 leaflets (occasionally 5, especially towards the base of the cane).

*Leaf attachment.*—Petiolate.

*Leaf orientation.*—Flat to pendant.

*Leaf size.*—An average of 18.8 cm in length and 17.6 cm in width.

*Leaf quantity.*—An average of 31.7 per cane.

*Leaflet shape.*—Broad.

*Leaflet base.*—Terminal leaflets; cordate to cuneate, lateral leaflets; oblique.

*Leaflet apex.*—Acute, occasionally acuminate.

*Leaflet venation.*—Pinnate, color primarily matches leaf color.

*Leaflet margins.*—Doubly serrate.

*Relative position of lateral leaflet.*—Non-overlapping to slightly overlapping at base.

*Profile of leaflet cross-section.*—Slightly concave.

*Leaflet arrangement*.—One terminal and 1 to 2 lateral pairs.

*Leaflet attachment*.—Sessile to stalked.

*Leaflet surface*.—Young leaf; weak, mature leaf; wavy.

*Leaflet color*.—Young leaf; upper surface 143A, lower surface 146B; mature leaf: upper surface 146A, lower surface 148B.

*Leaflet size*.—Terminal; an average of 12.1 cm in length and 8.9 cm in width, lateral; and average of 8.6 cm in length and 5.4 cm in width.

*Petioles*.—Round in shape, an average of 4.3 cm in length and 2.1 mm in width, color 145B, surface pubescent and with some spines and prickles.

*Rachis*.—Round in shape, an average of 2.7 cm in length and 1.4 mm in width, color; 145A with upper surface suffused with 173A with sun exposure and 173B with shade exposure, all surfaces pubescent and with occasional spines and prickles along the vascular lines.

Inflorescence description:

*Inflorescence*.—Raceme, an average of 8.2 cm in length (from base of petiole), average of 3.1 cm in length (from base of rachis) and 2.3 cm in width under first bud.

*Rachis* (*peduncle*).—Oval in shape, color 146D, glabrous surface, with some spines and prickles.

*Pedicels*.—Oval in shape, an average of 3.45 cm in length and 1.3 mm in width immediately under the bud, color 146D, surface glabrous with spines and prickles.

*Flower buds*.—Triangular in shape with a flat wide bottom and apex narrowing to a point, up to 7.82 mm (an average 6.71 mm) in width and 11.21 mm (an average 9.13 mm) in length, color 144B.

*Flower type*.—Spreading calyx with a center of a ring of numerous upright stamens and with numerous pistils in the center, petals are quickly shed upon opening.

*Flower number*.—An average of 4.5 per raceme.

*Flower size*.—Average of 8.6 mm in depth and 1.78 cm in diameter.

*Sepals*.—Five, an average of 8.68 mm in length and 5.11 mm in width, base aristate, apex acuminate, surface downy hair with some spines/prickles.

*Petals*.—Five, dropped at fruit maturity, an average of 8.3 mm in length and 2.99 mm in width with an average ratio between those measurements of 0.36, linear in shape with a rounded apex and oblong base, glabrous on upper and lower surfaces, thin, color during flowering 155C to 155A, occasional remaining petal when fruit is maturing typically 186B in color.

*Receptacle*.—An average 9.3 mm in diameter and 15.12 mm in depth, color at the base 158B and at the top 161C.

*Androecium*.—An average of 99 stamens that form a concentric ring about 9.1 mm in diameter, inserted into calyx at base, about 4.62 mm in length, filament color 156D, the color and amount of pollen was not observed.

*Gynoecium*.—An average of 105.8 pistils per flower, styles an average of 3.27 mm in length and 155B in color, stigmas are very small, ovaries are attached to receptacle at base, very small, ovate in shape.

Fruit description:

*General*.—The overall fruit is cohesive and with good skin strength so under normal manual harvest conditions the aggregates remain together and the skin intact so there is no free juice in the clamshells.

*Fruit number*.—An average of 15 per fruiting lateral.

*Fruit size*.—2.3 cm in length and 2.19 cm in width on average although a range of variability is possible in this trait depending on the period of record and whether terminal fruit are part of the average or recorded separately.

*Fruit shape*.—The aggregate fruit is blunt conical.

*Drupelets*.—There are an average of 98.44 drupelets per aggregate fruit which are globose in shape and firm, color when mature; 45A, surface is glossy, style and stigma; persistent at maturity, little dent in the middle.

*Persistence of bracts*.—Persistent.

*Receptacle*.—Conical to blunt conical in shape and, persistent on the plant at harvest, fleshy, size varies with individual fruit size, generally creamy in color (155 C) but showing varying shades of pink in fully ripe or overripe fruit (N155B to N155C).

*Fruit maturity date*.—So far in southern England this variety has been grown as a strict (mid-season) primocane that crops in the new cane between early September and late October or early November depending on weather conditions, typically, the 50% pick date (time by which 50% of the total crop has been harvested) falls in week 39, it is also possible to 'double crop' this variety (fruit harvested both from the primocane and floricane) both in the U.K. and southern Spain; in these circumstances cropping dates can be manipulated by cane and environmental management.

*Seed*.—Kidney shaped, 1 per drupelet, 2.3 mm in length, 1.4 mm in width, 164B and 164C in color.

*Cropping frequency*.—As described here, annually, produced on same year cane (primocanes) but the plants are able to also crop twice-annually; in the primocane in the first year of growth and following enforced or natural dormancy in the floricane.

*Flavor*.—Sweet, bit dry.

*Brix*.—10° to 10.5° under conditions grown.

*Fruit weight*.—Typically 7 g with means ranging from 9.4 g at the beginning of cropping (when more terminal fruit are present) to 5.0 g (towards the end of the fruiting season).

*Shelf life*.—When harvested optimally, fruits can be transported and kept in chilled conditions without noticeable deterioration for 6 or more days after picking.

It is claimed:

1. A new and distinct cultivar of *Rubus idaeus* hybrid plant named 'emr 20171' as herein illustrated and described.

* * * * *